United States Patent
Wakamiya et al.

[11] Patent Number: 6,056,974
[45] Date of Patent: May 2, 2000

[54] RAPID-RELEASE S1452 TABLETS

[75] Inventors: Eizo Wakamiya, Hyogo; Yoshikazu Suzuki, Osaka; Hitoshi Kadota, Hyogo, all of Japan

[73] Assignee: Shionogi & Co., Ltd., Osaka, Japan

[21] Appl. No.: 09/117,833

[22] PCT Filed: Apr. 11, 1997

[86] PCT No.: PCT/JP97/01260

§ 371 Date: Aug. 12, 1998

§ 102(e) Date: Aug. 12, 1998

[87] PCT Pub. No.: WO97/40828

PCT Pub. Date: Nov. 6, 1997

[30] Foreign Application Priority Data

Apr. 26, 1996 [JP] Japan ................................ 8-106533

[51] Int. Cl.[7] ............................................. A61K 9/20
[52] U.S. Cl. ........................ 424/464; 424/465; 424/468; 424/470; 424/477; 424/481; 424/500
[58] Field of Search ............................................. 424/464

[56] References Cited

U.S. PATENT DOCUMENTS

| | | |
|---|---|---|
| 4,665,018 | 5/1987 | Vold . |
| 4,666,703 | 5/1987 | Kopf . |
| 4,861,913 | 8/1989 | Narisada et al. . |
| 5,168,101 | 12/1992 | Arai et al. . |
| 5,270,055 | 12/1993 | Moest . |

FOREIGN PATENT DOCUMENTS

| | | |
|---|---|---|
| 56-152416 | 11/1981 | Japan . |
| 59-101423 | 6/1984 | Japan . |
| 63-115815 | 5/1988 | Japan . |
| 63-119426 | 5/1988 | Japan . |
| 63-139161 | 6/1988 | Japan . |
| 1-175936 | 7/1989 | Japan . |
| 2-160758 | 6/1990 | Japan . |
| 2-180862 | 7/1990 | Japan . |
| 3-17054 | 1/1991 | Japan . |
| WO 9740828 | 11/1997 | WIPO . |

OTHER PUBLICATIONS

Derwent, World Patent Index, Abstract 90–149201/20.
Derwent, World Patent Index, Abstract 85–250478/41.

*Primary Examiner*—Thurman K. Page
*Assistant Examiner*—Susan Tran
*Attorney, Agent, or Firm*—Birch, Stewart, Kolasch, & Birch, LLP.

[57] ABSTRACT

The present invention provides a rapid-release tablet of S1452 at least containing the following components:

a. a principal agent comprising (+)-(Z)-calcium 7-[(1R, 2S,3S,4S)-3-benzenesulfonaidobicyclo[2.2.1]hept-2-yl]-5-heptenoate dihydrate (S1452), and b. a dispersant in an amount enough to disperse the principal agent after the disintegration of the tablet.

11 Claims, 1 Drawing Sheet

RAPID-RELEASE S1452 TABLETS

This application is the national phase under 35 USC §317 of prior PCT International Application No. PCT/JP97/01260 which has an International filing date of Apr. 11, 1997 which designated the United States of America, the entire contents of which are hereby incorporated by reference.

TECHNICAL FIELD

The present invention relates to a rapid-release tablet of (+)-(Z)-calcium 7-[(1R,2S,3S,4S)-3-benzenesulfonamidobicyclo[2.2.1]hept-2-yl]-5-heptenoate dihydrate (hereinafter referred to as S1452). S1452 has been known to possess an antagonistic activity to thromboxane $A_2$ ($TXA_2$) receptor, thus the present preparation is useful as a medical preparation for diseases concerned with $TXA_2$.

BACKGROUND ART

Japanese Laid-Open Patent Publication No. 63-139161 describes that a series of bicycle sulfonamide derivatives including S1452 possess an antagonistic activity to $TXA_2$ receptor and is effective for the prevention or treatment of inflammation, hypertension, thrombosis, cerebral apoplexy, myocardial infarction, angina pectoris, cerebral infarction, asthma, and the like.

Japanese Laid-Open Patent Publication No. 2-160758 discloses the lysine salt corresponding to S1452.

Japanese Laid-Open Patent Publication No. 3-17054 describes that S1452 is stable crystal.

However, no embodiment of the preparation of S1452 is described in any of the above patent publications. Therefore, it has been desired to develop a medical preparation, especially tablets, with which S1452 can be suitably utilized as a medicine.

Additionally, a preparation containing silica (silicon dioxide) is described, for example, in Japanese Laid-Open Patent Publication Nos. 60-209518 and 2-178222, wherein the purpose of adding silica is to make tablets stabler in high-temperature storage, to prevent granules from adhering each other before coating them and the like, and so it is not related directly to the solubility of a principal agent in tablets. Namely, those technologies do not suggest the present invention at all.

DISCLOSURE OF INVENTION

Considering the above problems, the present inventors have studied on formulating S1452 into tablets. Usually, in order to enhancing the solubility of a principal agent in tablets, it is generally carried out to allow the principal agent to release at once by quickly disintegrating the tablets through the addition of disintegrators thereto. However, the present inventors have found that in the case of S1452 being formulated into tablets by merely adding disintegrator as usual, the solubility is well high at pH around neutral condition but remarkably low in an acidic solution. Therefore, it has been concerned that the dissolving of S1452 might be delayed in stomach when orally administered.

Then, the present inventors have further examined to find that the solubility of S1452 can be improved by adding, as an additive in preparing tablets, a dispersant in an amount enough to disperse the principal agent after the disintegration in a body.

BEST MODE FOR CARRYING OUT THE INVENTION

Figure 1:
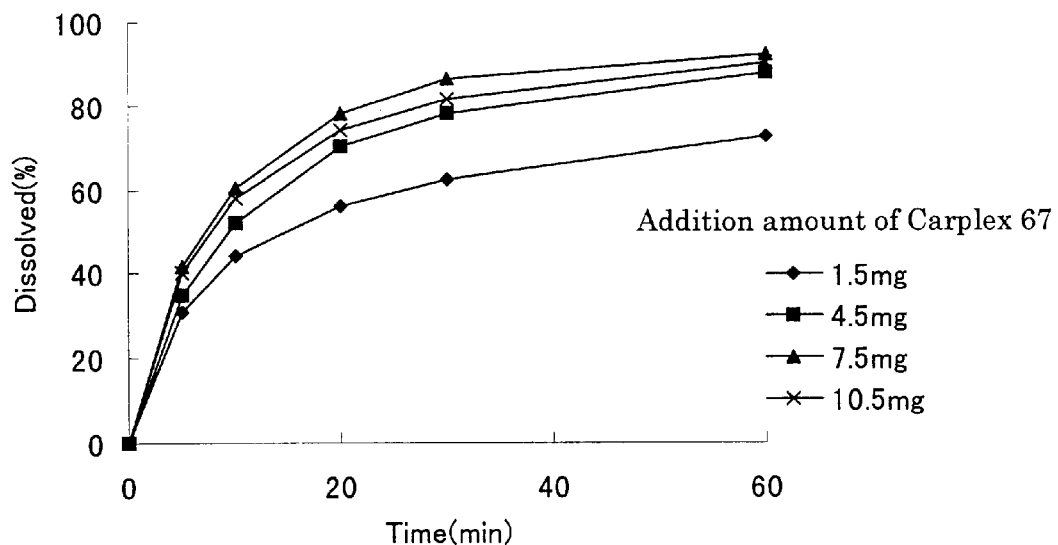
FIG. 1 shows, as to the tablet containing 25 mg of S1452, the relation between the amount of dispersants and the dissolving rate in an acidic solution. The axis of ordinate shows the dissolving rate (%) and the axis of abscissa shows the time (minute).

The present invention provides a rapid-release tablet of S1452 (hereinafter referred to as a tablet of the present invention ), which is characterized by at least containing the following components "a" and "b":

a. a principal agent comprising (+)-(Z)-calcium 7-[(1R, 2S,3S,4S)-3-benzenesulfonamidobicyclo[2.2.1]hept-2-yl]-5-heptenoate dihydrate (S1452), and b. a dispersant in an amount enough to disperse the principal agent after the disintegration of the tablet.

The preferred embodiments of a tablet of the present invention are exemplified below.

(1) A tablet of the present invention, wherein the amount of the dispersant is 0.05 to 9 parts by weight to 100 parts by weight of the tablet.

(2) A tablet of the present invention, wherein the amount of the dispersant is 0.1 to 7 parts by weight to 100 parts by weight of the tablet.

(3) A tablet of the present invention, wherein the amount of the dispersant is 0.3 to 5 parts by weight to 100 parts by weight of the tablet.

(4) A tablet of the present invention, wherein the amount of the dispersant is 0.5 to 30 parts by weight to the principal agent.

(5) A tablet of the present invention, wherein the dispersant is silica.

(6) A tablet of the present invention, which comprises as the dispersant 0.3 to 5 parts by weight of silica to 100 parts by weight of the tablet.

(7) A tablet of the present invention, which further comprises a disintegrator.

(8) A tablet of the present invention described in (7), wherein the amount of the integrator is 5 to 30 parts by weight to 100 parts by weight of the tablet.

(9) A tablet of the present invention described in (7), wherein the disintegrator is low-substituted hydroxypropylcellulose.

(10) A tablet of the present invention, which comprises 0.3 to 5 parts by weight of silica and 5 to 30 parts by weight of low-substituted hydroxypropylcellulose to 100 parts by weight of the tablet.

(11) A tablet of the present invention, wherein the dissolving rate of the principal agent is 70% or more at 60 minutes in an acidic solution.

(12) A tablet of the present invention, which further comprises an excipient and/or a binder.

(13) A tablet of the present invention described in (12), which comprises 40 to 90 parts by weight of the excipient and 0.5 to 5 parts by weight of the binder to 100 parts by weight of the tablet.

(14) A tablet of the present invention described in (12), wherein the excipient is lactose, mannitol, and/or starch.

(15) A tablet of the present invention described in (12), wherein the binder is hydroxypropylcellulose.

(16) A tablet of the present invention, wherein the surface is coated with a film base agent containing a polymer soluble in gastoric juice and a plasticizer.

(17) A tablet of the present invention described in (16), wherein the polymer soluble in gastric juice is a cellulose coating agent and the plasticizer is macrogol.

A tablet of the present invention is explained in more detail below.

As to S1452 of the principal agent, the particle size had better be small in the light of solubility, preferably the specific surface area is about 4000 cm$^2$/g or more, more preferably about 7000 to 10000 cm$^2$/g. Though the amount of the principal agent may be appropriately adjusted depending on the kind of diseases, the type of patients to be administered and the like, the range is usually about 1 to 30 parts by weight to 100 parts by weight of the tablet, preferably about 3 to 25 parts by weight. In the case of the concentration of the principal agent being too high, it is susceptible to change on standing and the solubility might be lowered. In the contrary case, the desired pharmacological effect can not be achieved.

The dispersant used in the present invention disperses S1452 of the principal agent after the disintegration in the digestive tract, especially in stomach, thereby enhancing the solubility. In more detail, S1452 is readily dissolved at pH value around neutral, however, the solubility tends to lower under acidic condition, especially at pH 4 or less. The reason is that S1452 dissociates Ca$^{2+}$ in an acidic solution to be an oily free acid (namely, (+)-(Z)-7-[(1R,2S,3S,4S)-3-benzenesulfonamidobicyclo[2.2.1]hept-2-yl]-5-heptenoic acid), and as a result, the surfaces of the tablet and particles produced by the disintegration are made glutinous and insoluble in water when S1452 is conventionally formulated into tablets. However, through the previous addition of the dispersant together with the principal agent, the agent-containing particles can be prevented from being contacted with each other after the disintegration, thereby the agent can slowly be released into a solution. As a result, the total amount of S1452 dissolved in stomach can be increased, for example, to the level of dissolving rate; about 70 to 95% at 60 minutes.

The dispersant usable in the present invention may be a pharmaceutical additive capable of dispersing the principal agent into a solution after the integration, which includes for example, silica (silicone dioxide), synthetic aluminum silicate, and the like, preferably silica such as Carplex® (#67, #80, CS-50 etc., Shionogi & Co., Ltd.), aerosil®. Though the dispersant is to be added enough to disperse the principal agent after the integration, the addition amount is extremely small to the total amount of the tablet, usually about 0.05 to 9 parts by weight, preferably about 0.1 to 7 parts by weight, more preferably about 0.3 to 5 parts by weight to 100 parts by weight of the tablet. In other words, the amount is usually about 0.5 to 30 parts by weight, preferably about 1 to 30 parts by weight to 100 parts by weight of S1452. In the case of the ratio of the dispersant being too low, the solubility of S1452 in gastric juice can not be improved. On the contrary, in the case of the ratio being too high, the contact of each drug particle can be prevented, while the solubility is lowered by the steric hindrance of an excess amount of the disperasnt existing around the surface of the drug, or the other trouble occurs such as powder scattering in the handling, thereby leading to undesirable results.

Preferably, a tablet of the present invention may contain a disintegrator for facilitating the disintegration. As the disintegrator, those well known in the present field may be used, for example, partly pregelatinized starch, sodium carboxymethyl starch, calcium carboxymethylcellulose, low substituted hydroxypropylcellulose (L-HPC), sodium croscarmellose (Ac-Di-Sol, Asahikasei), polyvinylpolypyrrolidone, and the like, preferably L-HPC. The amount of the disintegrator had better be enough to quickly disintegrate the tablet, for example, to complete the disintegration within several ten minutes, preferably several minutes in the first or second fluid regulated in the Japanese Pharmacopoeia, and usually, the amount is about 5 to 30 parts by weight, preferably about 10 to 25 parts by weight to 100 parts by weight of the tablet.

A tablet of the present invention may further contain an optional pharmaceutically acceptable additive such as an excipient, a binder, and a lubricant.

As the excipient, those well known in the technology field may be used, for example, lactose, sucrose, mannitol, corn starch, potato starch, hydroxypropyl starch, and the like, preferably lactose and starch. The amount of the excipient may appropriately be adjusted depending on the amount of the principal agent, the size of the objective tablet, and the like, which is usually about 40 to 90 parts by weight, preferably about 50 to 80 parts by weight to 100 parts by weight of the tablet.

As the binder, those well known in the technology field may be used, for example, methylcellulose, polyvinylpyrrolidone, hydroxypropylcellulose, polyvinyl alcohol, gelatin, dextrin and the like, preferably hydroxypropylcellulose (L-HPC). The amount of the binder is usually about 0.5 to 5 parts by weight, preferably about 1 to 3 parts by weight to 100 parts by weight of the tablet.

Examples of the lubricant include magnesium stearate, talc, sucrose aliphatic acid ester, and usually the amount is extremely small, for example, about 1 parts by weight to 100 parts by weight of the tablet.

A tablet of the present invention can be prepared with the above materials through steps of mixing, kneading, granulating, drying, adding lubricant, tableting, and the like, each according to the well known methods in this field.

As to the kneading, examples of the equipment include a brabender, a double screw kneader, a high speed mixer, and the like, and preferable is a stirring type such as a double screw kneader capable of relatively slow kneading, because it is desirable to sufficiently knead without causing excessive aggregation of the principal agent in the light of enhancing the solubility.

The tableting may be carried out by using a commercial tablet machine, usually under a pressure of about 0.7 to 1.2 ton.

The surface of a tablet of the present invention obtainable by the above method may be coated with a film base. The coating may be carried out according to the method well known in the field, for example, the coating with a film of about 20 to 30 μm in thickness by a commercial machine. The coating can improve the appearance or the physical and chemical stability of the tablet, or prevent or decrease unpleasant taste of drugs in mouth.

As the film base, suitably used is a polymer soluble in gastoric juice, such as cellulose coating agents, acrylate acid coating agents, polyvinylacetal diethylaminoacetate (AEA, Sankyo), aquacoat (FMC Co.), and the like.

Usually, the cellulose coating agents are relatively easy to coat with and have high water-solubility, which include, for example, hydroxypropylcellulose and hydroxypropylmethylcellulose (HPMC).

The acrylate acid coating agents can readily protect the surface of a tablet and give fine luster thereto, which include, for example, ethyl acrylate/methyl methacrylate copolymer (Eudragit RS, Röhm Co.), ethyl acrylate/butyl methacrylate/dimethylaminoethyl methacrylate copolymer (the same company). Preferable is cellulose coating agents, esp. HPMC which can fairly prevent the solubility of tablets from decreasing due to change on standing even after long period of storage.

The amount of the film base is usually about 1 to 5 parts by weight, preferably about 2 to 4 parts by weight to an naked tablet. In the case of the coating amount being too small, the physical or chemical stability of the obtained tablets might be lowered and unpleasant taste of the principal agent can not be reduced. On the contrary, an excess amount of the coating might bring a bad effect into the disintegration of tablets.

The film base may contain an optional additive such as a plasticizer, a light stabilizer, a lubricant, and the like.

Examples of the plasticizer include macrogol, triacetin, propylene glycol, and the like, preferable is macrogol. The amount is usually about 5 to 20 parts by weight to the amount of the film base, and the physical strength of tablets can be improved by controlling the amount.

Examples of the light stabilizer include titanium oxide and colorant, which amount is usually about 1 to 10 parts by weight to the film base.

Examples of the lubricant include talc, magnesium stearate, and polishing wax, which may be added in a very small amount if necessary.

EXAMPLES

Examples of preparations and experiments are explained below, which do not limit the scope of the present invention at all.

Examples 1 to 3

Each tablet ($\phi$=7 mm) containing ingredients shown in Table 1 was prepared by the following method.

Method for Preparation

Mixing, Kneading: double screw kneader (10 minutes mixing, 30 minutes kneading)

Granulating: power mill (screen: 3 mm herringbone, 2000 rpm)

Drying: side vented tray drier (50° C., 60 minutes)

Adjusting size of granule: power mill (screen: 30 mesh, 1500 rpm)

Adding lubricant: twin-shell blender (5 minutes)

Tableting: rotary tablet machine: (RTM-S30K-2S type, 40 rpm)

TABLE 1

(Unit: mg)

| Ingredient | Example No. | | |
|---|---|---|---|
| | 1 | 2 | 3 |
| S1452 | 5.0 | 10.0 | 20.0 |
| Lactose | 70.8 | 67.3 | 60.0 |
| Corn starch | 27.3 | 25.8 | 22.8 |
| L-HPC(LH31) | 20.0 | 20.0 | 20.0 |
| HPC(SL) | 1.3 | 1.3 | 1.3 |
| Carplex ® 67 | 1.3 | 1.3 | 1.3 |
| Magnesium stearate | 1.3 | 1.3 | 1.3 |
| Water | 3.0 | 3.0 | 3.0 |
| Total | 130.0 | 130.0 | 130.0 |

Examples 4 to 7

According to the same method as that of the above examples, tablets each containing 25 mg of S1452 and a different amount of the dispersant (Carplex® 67, SHIONOGI) were prepared ($\phi$=7 mm), provided that the dispersant was added together with lubricant. The ingredients are shown in Table 2.

TABLE 2

(Unit: mg)

| Ingredient | Example No. | | | |
|---|---|---|---|---|
| | 4 | 5 | 6 | 7 |
| S1452 | 25.0 | 25.0 | 25.0 | 25.0 |
| Lactose | 63.6 | 60.6 | 57.6 | 54.6 |
| Corn starch | 24.0 | 24.0 | 24.0 | 24.0 |
| L-HPC(LH31) | 30.0 | 30.0 | 30.0 | 30.0 |
| HPC(SL) | 3.0 | 3.0 | 3.0 | 3.0 |
| Carplex ® 67 | 1.5 | 4.5 | 7.5 | 10.5 |
| Magnesium stearate | 1.5 | 1.5 | 1.5 | 1.5 |
| Water | 1.4 | 1.4 | 1.4 | 1.4 |
| Total | 150.0 | 150.0 | 150.0 | 150.0 |

Examples 8 to 11

According to the same method as that of the above examples 1 to 3, tablets each containing 50 mg of S1452 were prepared ($\phi$=8 mm), which ingredients are shown in Table 3.

TABLE 3

(Unit: mg)

| Ingredients | Example No. | | | |
|---|---|---|---|---|
| | 8 | 9 | 10 | 11 |
| S1452 | 50 | 50 | 50 | 50 |
| Lactose | 88 | 88 | 88 | 90 |
| Corn starch | 38 | 37.5 | 37 | 39 |
| L-HPC(LH31) | 20 | 20 | 20 | 20 |
| HPC(SL) | 0 | 0.5 | 1 | 2 |
| Carplex ® 67 | 2 | 2 | 2 | 2 |
| Magnesium stearate | 2 | 2 | 2 | 2 |
| Ac-di-sol | 5 | 5 | 5 | 0 |
| Water | 5 | 5 | 5 | 5 |
| Total | 210 | 210 | 210 | 210 |

Examples 12 to 14

According to the same method as that of the above examples 1 to 3, tablets each containing 50 mg of S1452 and a different amount of the dispersant (Carplex® 67, SHIONOGI) were prepared ($\phi$=8 mm), which ingredients are shown in Table 4.

TABLE 4

(Unit: mg)

| Ingredient | Example No. | | | |
|---|---|---|---|---|
| | (Reference) | 12 | 13 | 14 |
| S1452 | 50 | 50 | 50 | 50 |
| Lactose | 89 | 88.5 | 89 | 88 |
| Corn starch | 39 | 39 | 38 | 38 |
| L-HPC(LH31) | 20 | 20 | 20 | 20 |
| HPC(SL) | 5 | 5 | 5 | 5 |
| Carplex ® 67 | 0 | 0.5 | 1 | 2 |

TABLE 4-continued (Unit: mg)

| Ingredient | Example No. | | | |
|---|---|---|---|---|
| | (Reference) | 12 | 13 | 14 |
| Magnesium stearate | 2 | 2 | 2 | 2 |
| Water | 5 | 5 | 5 | 5 |
| Total | 210 | 210 | 210 | 210 |

Example 15

Coating was carried out on the surface of the uncoated tablets (130 mg) obtained in Example 1, to form a film of 20 to 30 μm thick, whereby tablets of the present invention (133.5 mg) were obtained. The film base was prepared by dissolving into water 78.6 parts by weight of hydroxypropylmethylcellulose (HPMC), 14.3 parts by weight of macrogol 6000, and 7.1 parts by weight of titanium oxide.

Next explained are test examples of tablets of the present invention obtained above.

Disintegration and dissolution tests were carried out according to the methods regulated in the 12th revised Japanese Pharmacopoeia. The method of dissolution test is detailed below.

[Dissolution Test]

Test method: 2nd method (paddle method), stirring speed: 100 rpm

Test fluid: 1st Fluid (pH about 1.2), 2nd Fluid (pH about 6.8), and water each kept at 37±0.5° C.

Time: 5, 10, 20, 30, 60 (minutes)

Amount: 5 ml

Detection wave length: λ1=223 nm, λ2=300 nm

Experiment 1

The relation between the dissolving rate in an acidic solution and the amount of the dispersant (Carplex® 67, SHIONOGI) was examined with the tablets each containing 25 mg of S1452 which were obtained in Examples 4 to 7. The results are shown in Table 5 and FIG. 1.

TABLE 5

| | Example No. | | | |
|---|---|---|---|---|
| | 4 | 5 | 6 | 7 |
| Dispersant (mg) | 1.5 | 4.5 | 7.5 | 10.5 |
| Dissolving rate (%, at 60 minutes) | 72.4 | 87.7 | 92.1 | 90.2 |
| Rate of dispersant (W %) compared to | | | | |
| tablet | 1 | 3 | 5 | 7 |
| principal agent | 5.7 | 17 | 28.4 | 39.8 |

The above result shows that the dissolving rate in an acidic solution can be improved by increasing the amount of the dispersant. Particularly in the case of tablets containing 25 mg of S1452, it is possible to enhance the dissolving rate at 60 minutes to the level of 90% by containing the dispersant at about 5 to 7% by weight to the tablet or about 30% by weight to the principal agent. Any of the tablets were disintegrated within 5 minutes.

Experiment 2

Figure 2:
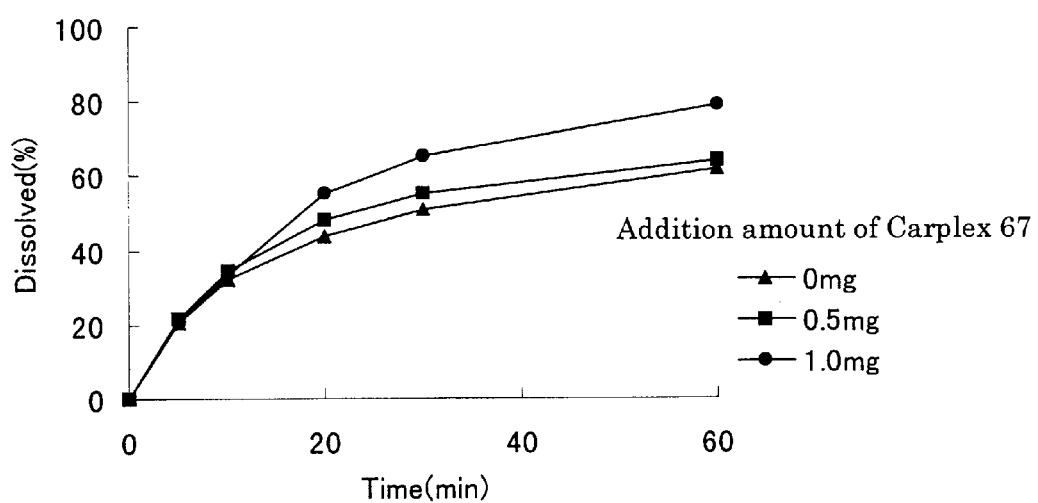
FIG. 2 shows, as to the tablet containing 50 mg of S1452, the relation between the amount of dispersants and the dissolving rate in an acidic solution The axis of ordinate shows the dissolving rate (%) and the axis of abscissa shows the time (minute).

The relation between the dissolving rate in an acidic solution and the amount of the dispersant (Carplex® 67, SHIONOGI) was examined with the tablets each containing 50 mg of S1452 which were obtained in Examples 12 and 13 and Reference 1. The results are shown in Table 6 and FIG. 2.

TABLE 6

| | Example No. | | |
|---|---|---|---|
| | (Reference) | 12 | 13 |
| Dispersant (mg) | 0 | 0.5 | 1 |
| Dissolving rate (%, at 60 minutes) | 61.8 | 64.1 | 79.1 |
| Rate of dispersant (W %) compared to | | | |
| tablet | 0 | 0.2 | 0.48 |
| principal agent | 0 | 1 | 2 |

The above result shows that the dissolving rate in an acidic solution can be improved by increasing the amount of the dispersant. Particularly in the case of tablets containing 50 mg of S1452, it is possible to enhance the dissolving rate at 60 minutes to the level of about 70 to 80% by containing the dispersant preferably at about 0.3% by weight or more to the tablet or about 1.5% by weight or more to the principal agent. Any of the tablets were disintegrated within 5 minutes.

Experiment 3

As to the film coated tablet of the present invention obtained in Example 15, the dissolving rate was determined with the 2nd Fluid which pH value (6.8) is around that of human saliva, for the purpose of examining the dissolving rate at the initial stage. The result indicates that the dissolving rate is extremely low that is, 0.4% at 30 sec. and 6% at 60 sec. Further, sensory evaluation was done with 5 panelists by putting the same tablets in their mouth for 30 seconds, and as a result, nobody felt bitter. Thus, it has been found that the film-coated type of tablet of the present invention is sufficiently controlled so as not to taste bitter.

Industrial Applicability

The present invention provides a rapid-release tablet of S1452. One of the character of the tablet is that the solubility of the principal agent in gasteric juice has been improved through the addition of a small amount of a dispersant, esp. silicate, as an additive. Further, film coating can physically and chemically strengthen the tablet and resolve the problem of uncomfortable taste originated from the principal agent. Particularly, it is possible to control the bitter taste of a tablet in mouth without decreasing the solubility, by selecting cellulose coating material as the film base.

We claim:

1. A rapid-release tablet at least containing the following components:

a. a principal agent comprising (+)-(Z)-calcium 7-[(1R, 2S,3S,4S)-3-benzenesulfonaidobicyclo[2.2.1]hept-2-yl]-5-heptenoate dihydrate, and b. a dispersant in an amount enough to disperse the principal agent after the disintegration of the tablet.

2. The tablet of claim 1, wherein the amount of the dispersant is 0.05 to 9 parts by weight to 100 parts by weight of the tablet.

3. The tablet of claim 1, wherein the amount of the dispersant is 0.1 to 7 parts by weight to 100 parts by weight of the tablet.

4. The tablet of claim 1, wherein the amount of the dispersant is 0.3 to 5 parts by weight to 100 parts by weight of the tablet.

5. The tablet of claim 1, wherein the dispersant is silica.

6. The tablet of claim 1, which comprises as the dispersant 0.3 to 5 parts by weight of silica.

7. The tablet of claim 1, which further comprises a disintegrator.

8. The tablet of claim 7, wherein the amount of the integrator is 5 to 30 parts by weight to 100 parts by weight of the tablet.

9. The tablet of claim 7, wherein the disintegrator is low-substituted hydroxypropylcellulose.

10. The tablet of claim 1, which comprises 0.3 to 5 parts by weight of silica and 5 to 30 parts by weight of low-substituted hydroxypropylcellulose to 100 parts by weight of the tablet.

11. The tablet of claim 1, wherein the dissolving rate of the principal agent is 70% or more at 60 minutes in an acidic solution.

* * * * *